United States Patent
Legrand et al.

(10) Patent No.: US 11,610,073 B2
(45) Date of Patent: Mar. 21, 2023

(54) DEVICE AND METHOD FOR ANALYZING THE STATE OF A SYSTEM IN A NOISY CONTEXT

(71) Applicants: THALES, Courbevoie (FR); UNIVERSITE DE BORDEAUX, Bordeaux (FR); INSTITUT POLYTECHNIQUE DE BORDEAUX, Talence (FR); Centre National de la Recherche Scientifique, Paris (FR)

(72) Inventors: Pierrick Legrand, Talence (FR); Eric Grivel, Talence (FR); Jean-Marc Andre, Talence (FR); Bastien Berthelot, Mérignac (FR)

(73) Assignees: THALES, Courbevoie (FR); UNIVERSITE DE BORDEAUX, Bordeaux (FR); INSTITUT POLYTECHNIQUE DE BORDEAUX, Talence (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 482 days.

(21) Appl. No.: 16/858,556

(22) Filed: Apr. 24, 2020

(65) Prior Publication Data
US 2020/0342199 A1 Oct. 29, 2020

(30) Foreign Application Priority Data
Apr. 26, 2019 (FR) ...................................... 1904422

(51) Int. Cl.
*G06F 17/15* (2006.01)
*G06K 9/00* (2022.01)
(Continued)

(52) U.S. Cl.
CPC .......... *G06K 9/0051* (2013.01); *A61B 5/7203* (2013.01); *G06F 17/15* (2013.01); *G06F 17/18* (2013.01)

(58) Field of Classification Search
None
See application file for complete search history.

(56) References Cited

U.S. PATENT DOCUMENTS

| 5,768,392 A | 6/1998 | Graupe |
| 8,543,195 B1 * | 9/2013 | Brockway ................ A61B 5/30 600/509 |

(Continued)

FOREIGN PATENT DOCUMENTS

| CN | 107 132 033 A | 9/2017 |
| WO | 2017/132225 A1 | 8/2017 |

OTHER PUBLICATIONS

Peng, et al., "Mosaic organization of DNA nucleotides", Physical Review, vol. 49, No. 2, pp. 1685-1689, 1994.
(Continued)

*Primary Examiner* — Craig C Dorais
(74) *Attorney, Agent, or Firm* — BakerHostetler

(57) ABSTRACT

A computer-implemented method for determining the state of a system, which includes steps of: collecting data relating to a system, the data being noisy data comprising data of interest and noise; generating a signal to be analyzed from the collected data, the signal being a noisy signal comprising a signal of interest and noise; analyzing the regularity of the signal of interest by compensating the influence of the noise in the computation of the power of the difference between the integrated noisy signal and its trend; and determining the state of the system depending on the result of the analysis of the regularity of the signal of interest.

15 Claims, 7 Drawing Sheets

(51) Int. Cl.
    *A61B 5/00*     (2006.01)
    *G06F 17/18*     (2006.01)

(56) References Cited

U.S. PATENT DOCUMENTS

| | | | |
|---|---|---|---|
| 10,153,806 B1* | 12/2018 | Petre | G06N 3/08 |
| 2014/0200823 A1* | 7/2014 | Zeng | A61B 5/30 |
| | | | 702/19 |
| 2019/0022791 A1* | 1/2019 | D'Angelo | G06F 17/16 |

OTHER PUBLICATIONS

Kantelhardt, et al., "Detecting long-range correlations with detrended fluctuation analysis", Physica A: Statistical Mechanics and its Applications, No. 1295, pp. 441-454, 2001.
Stadnitski, et al., "Measuring fractality", Frontiers in Physiology, vol. 3, Jan. 1, 2012.
Liu, et al., "ECG Noise Cancellation Based on Grey Spectral Noise Estimation", Sensors, vol. 19, No. 4, Feb. 15, 2019.
Singh, "Adaptive noise cancellation", Jan. 1, 2011.
Banerfjee, et al., "A cross wavelet transform based approach for ECG feature extraction and classification without denoising", Conference: 2014 International Conference on Control, Instrumentation, Energy and Communication (CIEC), pp. 162-165, 2014.
Osborn, "Moving average detrending and the analysis of business cycles", Oxford Bull. Econom. Statist, No. 157, pp. 547-558, 1995.

\* cited by examiner

DEVICE AND METHOD FOR ANALYZING THE STATE OF A SYSTEM IN A NOISY CONTEXT

CROSS-REFERENCE TO RELATED APPLICATIONS

This application claims priority to foreign French patent application No. FR 1904422, filed on Apr. 26, 2019, the disclosure of which is incorporated by reference in its entirety.

FIELD OF THE INVENTION

The invention is in the field of analyzing the state of a system, and the invention relates in particular to a device and to a method for compensating the influence of an additive noise when analyzing the regularity of a signal.

BACKGROUND

In a given environment, it may be necessary to have information about the psycho-physiological state of a person or the state of damage of an apparatus (metal structure, part of an engine, bridge, etc.). For this purpose, a set of sensors gathers information from the person or from the apparatus and delivers signals that, after being analyzed, make it possible to confirm and classify the state of the person or of the apparatus.

Features are extracted from the signals originating from the sensors. These features may characterize the statistical, temporal or frequency properties of the temporal series that are studied.

However, signals originating from sensors are disturbed by a measurement noise that may modify the information of interest and the value of the extracted features, and therefore lead to detrimental consequences regarding their use.

A particular feature relates to the temporal analysis of the signal, including notably its regularity, denoted 'a'. The latter transcribes a behavioural invariance of the signal to a change of time scale. In order to ascertain the regularity of a signal, it is common to estimate the Hurst index or coefficient, denoted 'H'.

Now, known methods for estimating the Hurst coefficient, such as the method called "detrended fluctuation analysis" (DFA) or the method called "detrending moving average" (DMA), provide an incorrect estimation of the feature when the signals are subjected to noise interference. Noise may be for example white noise or additive noise.

In order to overcome this problem, one approach may be that of enhancing the signal in order to eliminate the noise, and then estimating the regularity on the enhanced signal. However, the signal enhancement techniques that are conventionally employed, for example in speech processing, which are based on Kalman approaches or spectral subtraction approaches or that are based on wavelets, do not give satisfactory results. Specifically, the signal enhancement step increases the computational complexity and the computing time, this being detrimental in monitoring applications, in which real-time aspects are essential. In addition, this signal enhancement (or noise removal) step distorts the estimation of the regularity of the signal of interest in that the estimated value of a on the enhanced signal is distorted thereby. The known signal enhancement techniques do not make it possible to retain a correct estimation of the regularity of the signal of interest.

It is therefore necessary to implement feature estimation methods that are robust to the additive noise. The present invention addresses this need.

SUMMARY OF THE INVENTION

One subject of the present invention is a method for estimating the regularity of a signal of interest in a noisy context.

Another subject of the present invention is a device that comprises means for implementing a method for estimating the regularity of a signal of interest in a noisy context.

The invention will be applied to advantage in all fields, including for example the (bio)medical field where the analysis of the psycho-physiological state of a person is required, but also in all industrial fields requiring monitoring of parts, be this in the aeronautical industry, the automotive industry, the rail industry or any other heavy industry.

In order to achieve the desired results, methods, devices and a computer program product are claimed according to various embodiments.

What is proposed in particular is a computer-implemented method for determining the state of a system. The method comprises steps of:
collecting data relating to a system, said data being noisy data comprising data of interest and noise;
generating a signal to be analyzed from the collected data, said signal being a noisy signal comprising a signal of interest and noise;
analyzing the regularity of the signal of interest based on the noisy signal by compensating the influence of the noise in the computation of the power of the difference between the integrated noisy signal and its trend; and
determining the state of said system depending on the result of the analysis of the regularity of the signal of interest.

According to some embodiments of the method, as an alternative or in combination:
the step of analyzing the regularity of the noisy signal comprises the steps of: defining a set of values of 'N':
  for each value of 'N':
    computing the value of the power of the difference between the integrated noisy signal and its trend relative to the value 'N' from the autocorrelation function of the noisy signal;
    computing the value of the power of the difference between the integrated signal of interest and its trend from the autocorrelation function of the signal of interest; and
    estimating the regularity of the signal of interest.
the method comprises, after the step of generating a signal to be analyzed, a step of computing the autocorrelation function of the noisy signal.
the step of computing and compensating the value of the power of the difference between the integrated signal of interest and its trend comprises the steps of:
  estimating the properties of the noise;
  computing an autocorrelation function of the noise;
  computing an autocorrelation function of the signal of interest from the autocorrelation function of the noise and from the autocorrelation function of the noisy signal; and
  using the autocorrelation functions to mathematically compensate the influence of the noise in the computation of the value of the power of the difference between the integrated signal of interest and its trend.
the step of estimating the properties of the noise consists in studying the stationarity and/or the colored or white nature of the noise and/or representing it through a parametric model.

the step of defining a set of values of 'N' consists in dividing the noisy signal into segments of size 'N' and the step of estimating the regularity of the signal of interest may consist in including the estimation of the trend of the integrated noisy signal for the set of values of 'N'.

the step of defining a set of values of 'N' consists in applying a low-pass filter of order 'N' to the integrated noisy signal and the step of estimating the regularity of the signal of interest may consist in including the estimation of the trend of the integrated noisy signal.

the step of collecting the data consists in collecting data from sensors coupled to the system.

the sensors are configured so as to collect data relating to the electrical activity of the brain (EEG) "electroencephalogram" and/or to the electrical activity of the heart (ECG) "electrocardiogram" and/or to the electrodermal activity and/or to pupillometry.

the sensors comprise at least one inertial sensor that comprises accelerometers and gyrometers.

the method additionally comprises a step of displaying the state of said system depending on the result of the regularity analysis.

The invention also covers a computer program product, said computer program comprising code instructions for performing the steps of the claimed method when the program is executed on a computer.

The invention additionally covers a device for determining the state of a system, the device comprising:
  means for collecting data relating to a system, said data being noisy data comprising data of interest and noise;
  means for generating a signal to be analyzed from the collected data, said signal being a noisy signal comprising a signal of interest and noise;
  means for analyzing the regularity of the signal of interest based on the noisy signal by compensating the influence of the noise in the computation of the power of the difference between the integrated noisy signal and its trend; and
  means for determining the state of said system depending on the result of the regularity analysis.

According to one embodiment, the device additionally comprises a user interface configured so as to provide the state of the system.

BRIEF DESCRIPTION OF THE DRAWINGS

Various aspects and advantages of the invention will appear in support of the description of one preferred, but nonlimiting, mode of implementation of the invention, with reference to the figures below in which.

DETAILED DESCRIPTION

Figure 1:
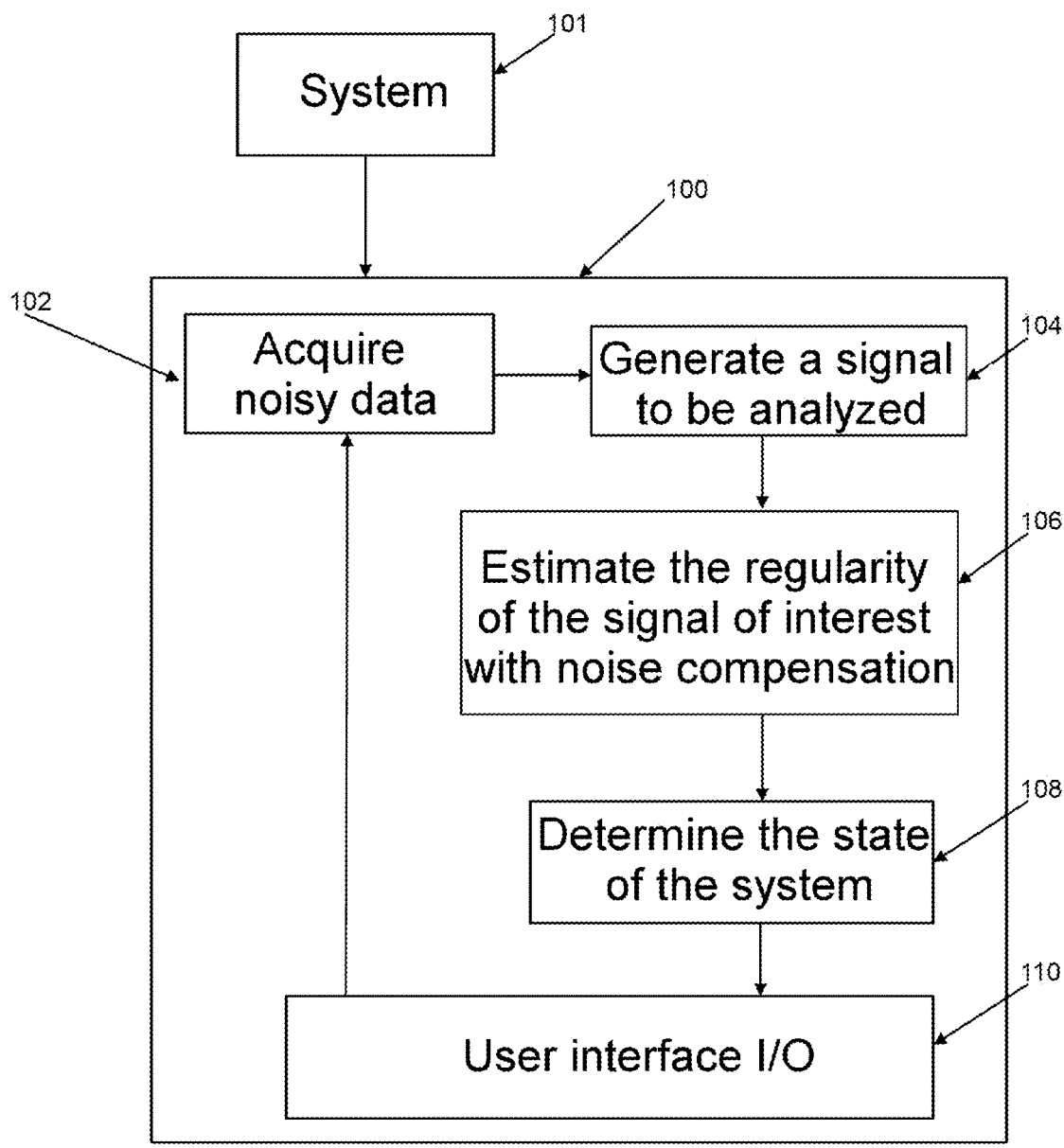
FIG. 1 is a block diagram illustrating one implementation of the device of the invention according to one embodiment.

FIG. 1 shows an implementation of the device (100) of the invention according to one embodiment. The device (100) generally comprises a data acquisition module (102) configured so as to receive data from at least one sensor able to record information about a monitored system (101), a signal generation module (104) configured so as to generate a signal to be analyzed from the acquired data, an analysis module (106) configured according to the principles of the invention so as to estimate the regularity of a signal of interest from the noisy signal, and a results module (108) coupled to the analysis module, configured so as to determine the state of the system from the results of the analysis. The system additionally comprises a user interface (110) configured so as to provide the result of the analysis. The user interface may advantageously be configured so as to parameterize the data acquisition module as needed.

The designation of a monitored system in the context of the present invention should be understood as being able to be a person or an apparatus to be monitored.

The designation of at least one sensor in the context of the present invention is not limiting in terms of the number and nature of sensors. Thus, one or a plurality of sensors may be implemented in order to record information about the monitored system.

If the monitored system is a person, for the purpose of ascertaining for example the attention level or drowsiness of said person, the sensors may be electrodes installed on the person in order to record information relating to the electrical activity of the brain (EEG) "electroencephalogram" and/or to the electrical activity of the heart (ECG) "electrocardiogram" and/or to the electrodermal activity and/or to pupillometry.

If the monitored system is an apparatus, for the purpose of ascertaining for example the level of damage thereto, the sensors may make it possible to study forces applied to said apparatus and the vibrations that it experiences. In one embodiment, the sensor may be an "inertial measurement unit" (IMU) inertial sensor that comprises accelerometers and gyrometers that also make it possible to track the evolution of the position of the object in space.

The data acquisition module (102) is configured so as to receive and record data originating from the sensors. The transmission of the data from the sensors may be either wired or wireless. As explained in the section about the prior art, signals originating from sensors are generally impacted by measurement noise, noise linked to the measurement context (environment, sensors). The acquired data are then noisy data comprising data of interest and noise.

The signal generation module (104) is configured so as to generate a temporal series from the acquired data. According to some embodiments, the data may be formatted, filtered and combined in order to generate a signal to be analyzed. Since the acquired data are impacted by an additive measurement noise, the signal to be analyzed that is generated is a noisy signal consisting of the signal of interest and additional noise.

The analysis module (106) is configured so as to estimate the regularity of the signal of interest according to the principles of the invention. Advantageously, the method of the invention makes it possible to compensate the influence of noise on the estimation of the regularity of the available noisy signal.

The module (108) for determining the state of the system is coupled to the regularity estimation module in order to determine the state of the monitored system according to the provided result.

The device of the invention comprises a user interface (110). The user interface may be configured so as to parameterize the data acquisition module (102). The user interface may be graphical in order to view the results obtained by the module (108) for determining the state of the system. The user interface may comprise additional means for generating the results audibly, for example.

The device of the present invention may be implemented using software and/or hardware elements. The method that is performed may be available in the form of a computer program product on a computer-readable medium. The medium may be electronic, magnetic, optical or electromagnetic. If the invention is implanted in a reprogrammable computing machine (for example an FPGA circuit), the corresponding program (that is to say the sequence of instructions) may be stored in or on a storage medium that is removable (for example an SD card or a mass storage means, such as a hard disk, for example an SSD) or that is non-removable, that is volatile or non-volatile, this storage medium being readable in part or in full by a computer or a processor. The computer-readable medium may be transportable or communicable or mobile or transmissible (i.e. via a 2G, 3G, 4G, WiFi, BLE, fibre-optic or other telecommunications network).

In terms of hardware, the computer for performing the described method may be implemented on a tablet or portable computer. By way of example of hardware architecture appropriate for implementing the invention, a device may include a communication bus to which a central processing unit (CPU) or microprocessor are connected, which processor may be "multicore" or "manycore"; a read-only memory (ROM) able to contain the programs necessary for implementing the invention; a random access memory (RAM) or cache memory containing registers suitable for recording variables and parameters that are created and modified during the execution of the abovementioned programs; and an I/O ("input/output") or communication interface suitable for transmitting and for receiving data.

Figure 2:
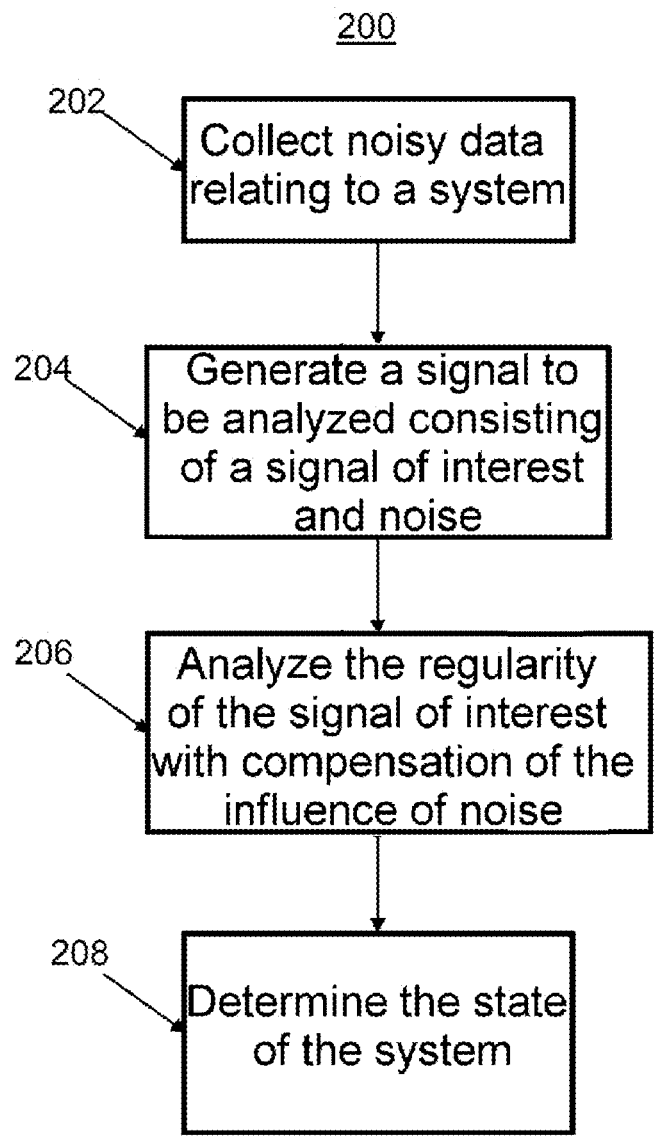
FIG. 2 illustrates a sequence of steps of the method of the invention according to one embodiment.

FIG. 2 illustrates a sequence of steps (200) for determining the state of a system according to the principles of the invention. In a first step (202), the method makes it possible to collect a plurality of data from the sensor or sensors used to monitor a system. According to one embodiment of the invention, the data are recorded by the data acquisition module (102) of the device (100) of FIG. 1. The acquired data comprise data of interest and noise.

In a following step (204), the method makes it possible to generate a signal from all or some of the acquired data. Since the collected data are noisy, the signal that is generated is a noisy signal consisting of the signal of interest and noise. The aim is to estimate the regularity of the signal of interest from the noisy signal.

A person skilled in the art is aware of various methods for analyzing the regularity of a signal, which belong to two large families:

that of estimators based on frequency analysis of the signal, including for example the local Whittle method, the periodogram method, the method based on wavelet transforms or else the semi-parametric method. More recently, solutions based on "empirical mode decomposition" (EMD) or fractional Fourier transform have been introduced.

that of estimators based on temporal analysis of the signal, including for example the analysis called "rescaled range", the "aggregated variance" method, the "absolute value" method or else the variance of the residual method.

The method of the invention falls within the family of the temporal analysis of a signal, by estimating the Hurst coefficient 'H'. Before describing the claimed method in detail, a reminder is given of known approaches for estimating the Hurst coefficient of a monofractal process.

One standard method of "fluctuation analysis" (FA) was proposed at the beginning of the 1990s. The principle is as follows: after integrating a signal to be analyzed, leading to a new sequence '$y_{int}$', the following variable is computed for various values of 'l':

$$F_{FA}(l) = \sqrt{\langle (y_{int}(i+1) - y_{int}(i))^2 \rangle}, \text{ where } \langle . \rangle \text{ represents the temporal mean.}$$

Since $F_{FA}(l) \propto l^{(H+1)}$ where a represents a proportionality relationship, $\log(F_{FA}(l))$ may be represented as a function of $\log(l)$ in order to estimate the value of 'H', which is then equal to the value of the slope of the obtained regression line minus 1.

More recently, two methods derived from the method (FA) have been widely used to estimate the Hurst coefficient: the method called "detrended fluctuation analysis" (DFA) and the method called "detrending moving average" (DMA).

The DFA method is described by C. K. Peng, S. V. Buldyrev, S. Havlin, M. Simons, H. E. Stanley and A. L. Goldberger in "Mosaic organization of DNA nucleotides" Physical Review, no. 149, pp. 1685-1689, 1994.

The DMA method is described by D. Osborne in "Moving average detrending and the analysis of business cycles" Oxford Bull. Econom. Statist, no. 157, pp. 547-558, 1995.

These two approaches are based on one and the same principle, which is that of estimating the trend of the integrated signal relative to a variable 'N' in order to obtain the power of the difference between the integrated signal and the trend. Although the principle is the same for the two methods, the way in which the trend is estimated differs depending on the approach, as does the definition of 'N'.

For the DFA method, estimating the trend of the integrated signal is based on splitting the signal into segments of size 'N' whose local trend is estimated. The global trend is then the concatenation of the local trends. For the DMA method, the parameter 'N' corresponds to the order of the low-pass filter that is applied to the integrated signal in order to obtain the trend thereof.

The steps of analyzing the regularity of a signal using the DFA and DMA approaches are recalled below.

Considering 'M' successive samples $\{y(m)\}_{m=1,\ldots,M}$ of a signal 'y', each method comprises four main steps:

Step 1: The signal is integrated and its mean value is subtracted therefrom. This step results in a new signal called "the profile of y" and is denoted:

$$y_{int}(m) = \sum_{i=1}^{m} (y(i) - \mu_y)$$

Step 2: The trend of the profile is estimated.

Figure 5:
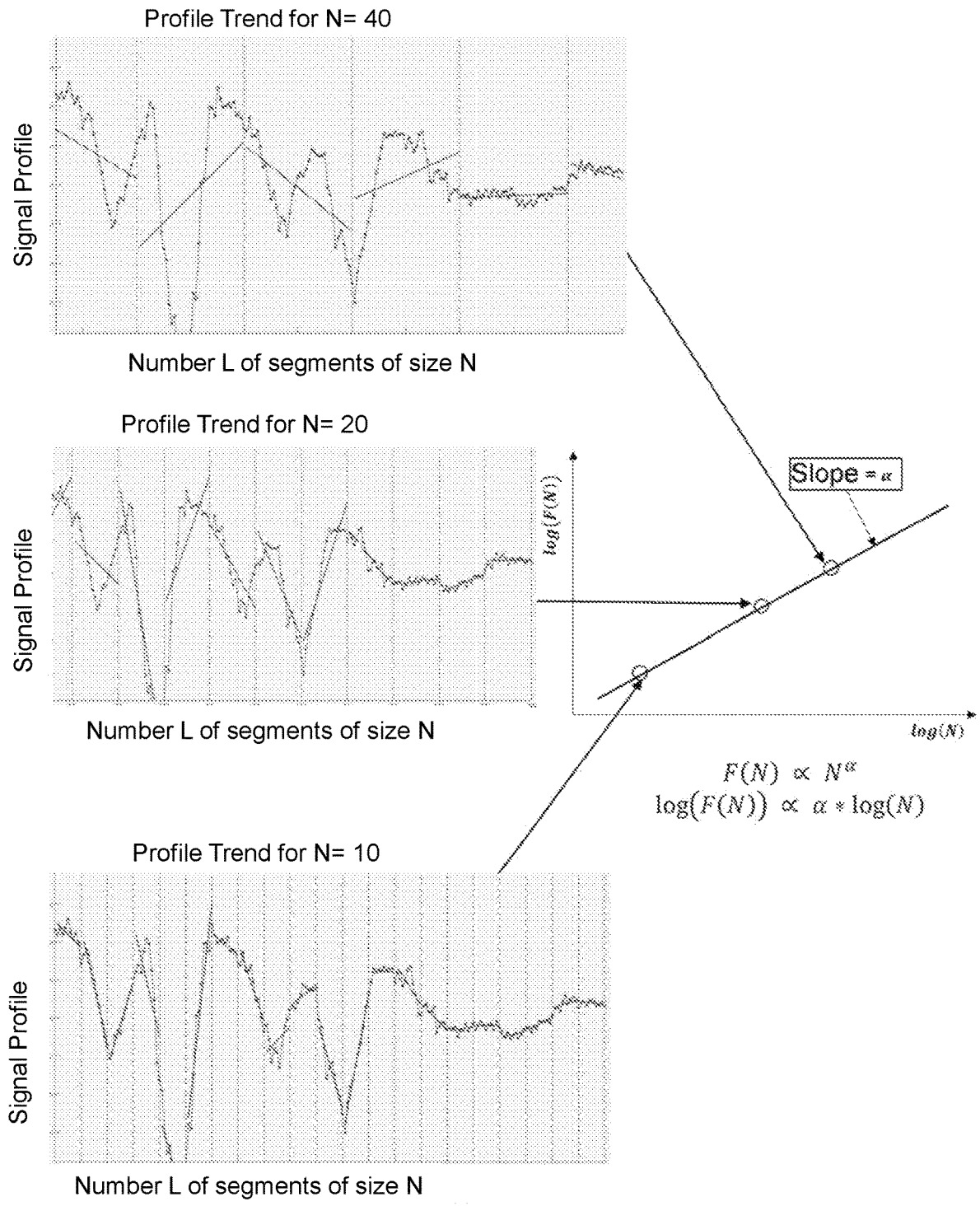
FIG. 5 is a depiction of the slope of the regression of points obtained from various trends of a given signal, in the case in which said signal is not noisy.

In the case of the DFA method, the profile is divided into 'L' segments of size 'N'. Since 'M', the number of successive samples, is not necessarily a multiple of 'N', only the L×N first samples are considered. The l-th local trend (l=1, . . . ,L) is estimated on the segment l in the least squares sense. The global trend of the integrated signal is then defined as the concatenation of the L local trends. One example of profile trends is illustrated on the left-hand portion of FIG. 5 for various values of N=(10, 20, 40).

In the case of the DMA method, the signal is filtered using a low-pass filter dependent on 'N'. Specifically, the impulse response of the filter is defined by $$h_{DMA}(n) = \frac{1}{N}$$

for n=0, . . . ,N−1.

Step 3: The global trend that is obtained is subtracted from the profile. A variable F(N) is then computed as the square root of the power of the difference between the integrated signal and its global trend relative to N.

Step 4: Steps 2 and 3 are repeated for various values of N. Since $F(N) \propto N^\alpha$ with $\alpha=H+1$ due to the integration of the signal, log(F(N)) is shown as a function of log(N). The value of the slope of the regression of the obtained points is then an estimation of α and therefore of the regularity of the signal. A depiction of a regression line obtained from three profile trends is illustrated on the right-hand part of FIG. 5.

These two DFA and DMA approaches, which have been widely applied in the biomedical field to study pathologies in voice, EEG and ECG signals, have demonstrated good performance in estimating the Hurst coefficient. Their use remains more limited in other fields, such as in an industrial context. In meteorology, one example is patent application WO2017/132225 A1 "Weather-based industry analysis system".

There are variants to these approaches whose purpose is to make corrections thereto. For the DFA method, mention may be made for example of DFAs of an order greater than 1, or else of "Adaptative Fractal Analysis" (AFA), or mention may be made of J. W. Kantelhardt, E. Koscielny-Bunde, H. H. A. Rego, S. Havlin and A. Bunde in "Detecting long-range correlations with detrended fluctuation analysis", Physica A: Statistical Mechanics and its Applications, no. 1295, pp. 441-454, 2001, which proposes a study aimed at adding a corrective term for small values of N.

For the DMA method, mention may be made of the variants "centred DMA", "weighted DMA of order l" (WDMA-l), "weighted centred DMA of order l" (WCDMA-l).

It appears that, in the known application contexts, signal enhancement techniques do not allow the regularity of the signal to be retained. Advantageously, the method of the present invention does not enhance the signal in order to eliminate noise, and then estimate the regularity of the signal of interest, but directly estimates the regularity of the signal of interest from the noisy signal by taking into consideration the influence of additive measurement noise, without losing the information of interest or changing the regularity of the signal. The method of the invention dispenses with the signal enhancement step in usual methods, so as to directly compensate the influence of measurement noise in the computation of the power of the difference between the integrated noisy signal and its trend.

Thus, returning to FIG. 2, analyzing the noisy signal according to the present invention consists in estimating (206) the regularity of the signal of interest with direct compensation of the influence of measurement noise in the analysis.

In a following step (208), the method makes it possible to determine the state of the system depending on the result of the analysis of the regularity of the signal of interest.

Figure 3:
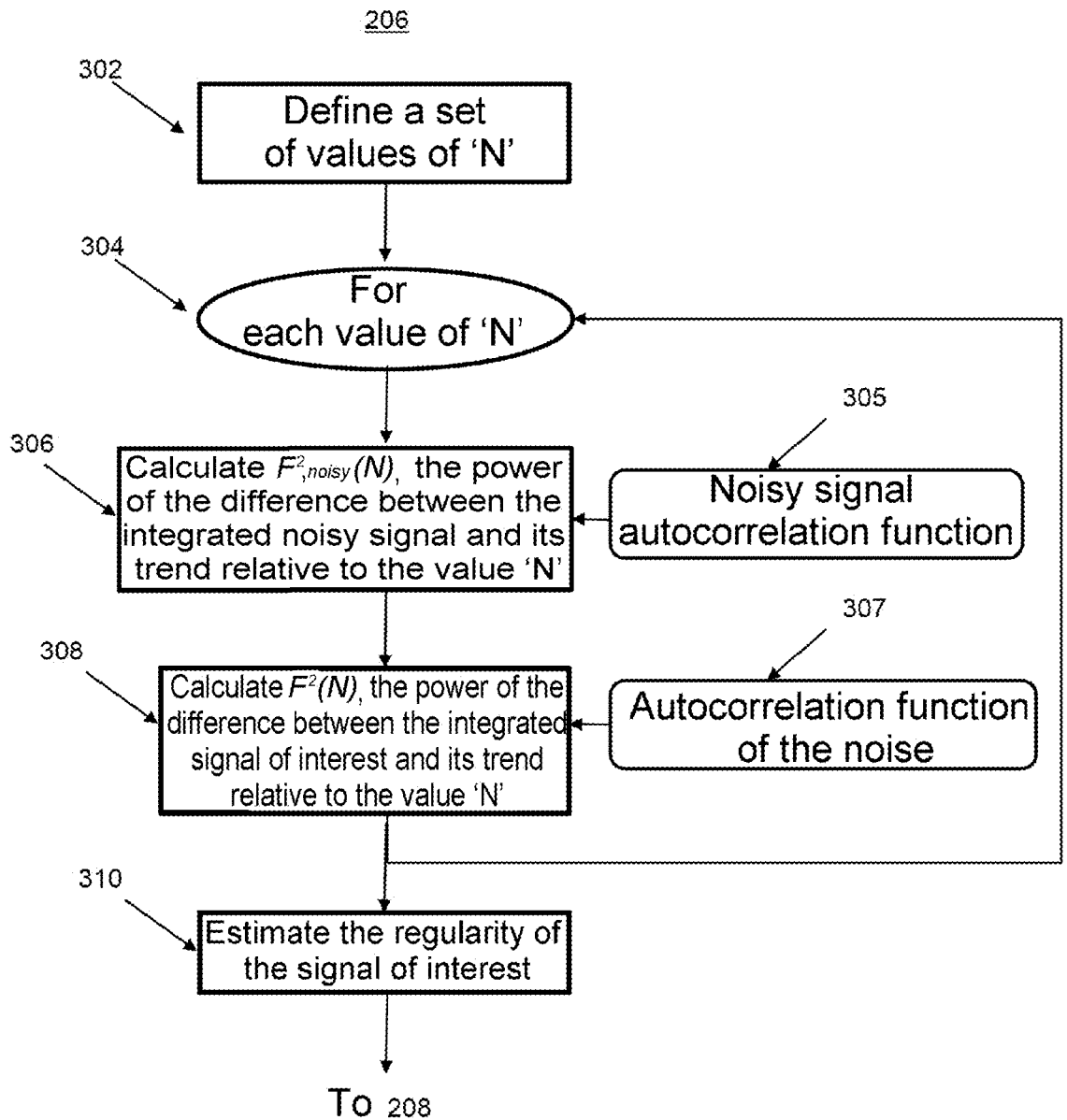
FIG. 3 illustrates a sequence of steps for estimating the regularity of a signal of interest, according to one embodiment of the invention.

FIG. 3, which describes step (206), illustrates a sequence of steps for estimating the regularity of a signal of interest from a noisy signal with compensation of the influence of noise, according to one embodiment of the invention based on the DFA method. However, the method may be transposed to any other regularity estimation method that would be based on computing a trend of the signal.

The method makes it possible, in a first step (302), to define a set of values of N, corresponding to a division of the noisy signal into segments of size 'N', and will then reiterate (304) a plurality of steps (306 to 308) for each value of N.

In the conventional DFA approach, F.(N) is defined by the following equation:

$$F.(N) = \sqrt{\sum_{l=1}^{L}\sum_{n=1}^{N}(yint((l-1)N+n) - x_l(n))^2}$$

where $x_l(n)$ is the n-th sample of the l-th local trend.

It is also possible to express F.(N) using the following equation:

$$F.^2(N) = \sum_{k=1}^{LN}\Gamma_{N,\cdot}(k,k)y^2(k) + 2\sum_{r=1}^{LN-1}\sum_{k=1}^{LN-r}r_{N,\cdot}(k,k+r)y(k)y(k+r)$$

where $\Gamma_{N,\cdot}(k,k+r)$ denotes the element of the matrix $\Gamma_N$, situated on row k and on column k+r and where $F.^2(N)$ corresponds to the power of the difference between the integrated signal of interest and its trend in relation to the chosen method (DFA, DMA, etc.) and $\Gamma_N$, is an appropriate matrix.

In step (306), the method makes it possible to compute $F.^2_{noisy}(N)$, the value of the power of the difference between the integrated noisy signal and its trend relative to the current value 'N'. This consists in expressing F.(N) as a function of the samples of the noisy signal: z(k)=y(k)+b(k)

Given the mathematical development above, the value of the power of the difference between the integrated noisy signal and its trend relative to the current value 'N', denoted $F.^2_{noisy}(N)$, may be expressed as follows:

$$F.^2_{noisy}(N) = \sum_{k=1}^{LN}\Gamma_{N,\cdot}(k,k)z^2(k) + 2\sum_{r=1}^{LN-1}\sum_{k=1}^{LN-r}\Gamma_{N,\cdot}(k,k+r)z(k)z(k+r)$$

This expression may be approximated using the autocorrelation function of the noisy signal (305).

Specifically, mathematically, it is possible to write:

$$E[F.^2_{noisy}(N)] = \sum_{k=1}^{LN}\Gamma_{N,\cdot}(k,k)E[z^2(k)] + 2\sum_{r=1}^{LN-1}\sum_{k=1}^{LN-r}\Gamma_{N,\cdot}(k,k+r)E[z(k)z(k+r)]$$

where E[ ] is the mathematical expectation operator. Due to this, in the case of a stationary process in the wide sense, this equation becomes:

$$E[F_{\cdot,noisy}^{2}(N)] = \sum_{k=1}^{LN}\Gamma_{N,\cdot}(k,k)R_{z,z}(0) + 2\sum_{r=1}^{LN-1}\sum_{k=1}^{LN-r}\Gamma_{N,\cdot}(k,k+r)R_{z,z}(r)$$

Finally, for a wide sense stationary and ergodic process, it is possible to approximate the value of $F_{\cdot,noisy}^{2}(N)$ with $E[F_{\cdot,noisy}^{2}(N)]$. A person skilled in the art understands that this is tantamount to approximating the product $z(k)z(k+r)$ with the autocorrelation $R_{z,z}(r)$ taken for a delay r with $r=0, \ldots, LN-1$.

In this case, it becomes:

$$F_{\cdot,noisy}^{2}(N) \approx \underbrace{\sum_{k=1}^{LN}\Gamma_{N,\cdot}(k,k)\hat{R}_{z,z}(0) + 2\sum_{r=1}^{LN-1}\sum_{k=1}^{LN-r}\Gamma_{N,\cdot}(k,k+r)\hat{R}_{z,z}(r)}_{\hat{F}_{\cdot,noisy}^{2}(N)} =$$

where $\hat{R}_{z,z}$ is the estimate of the autocorrelation function of the noisy signal.

This expression may be rewritten using the following equation:

$$\hat{F}_{\cdot,noisy}^{2}(N) = Tr(\Gamma_{N,\cdot})\hat{R}_{z,z}(0) + 2\sum_{r=1}^{LN-1} Tr(\Gamma_{N,\cdot}, r)\hat{R}_{z,z}(r)$$

In which $Tr(\Gamma_{N,\cdot}, r)$ denotes the trace of the rth diagonal of $\Gamma_{N,\cdot}$.

In the following step (308), the method makes it possible to compute the value of the power of the difference between the integrated signal of interest $\hat{F}^{2}(N)$ by compensating the contribution of noise in the computation, using the autocorrelation function of the signal of interest (307), as described by the description of FIG. 4.

Steps 306 to 308 are repeated for each value of N, and when all of the values of N values are processed, the method makes it possible, in a following step (310), to estimate the regularity of the signal of interest from the noisy signal, and then to continue with the step of determining the state of the system (208).

Figure 4:
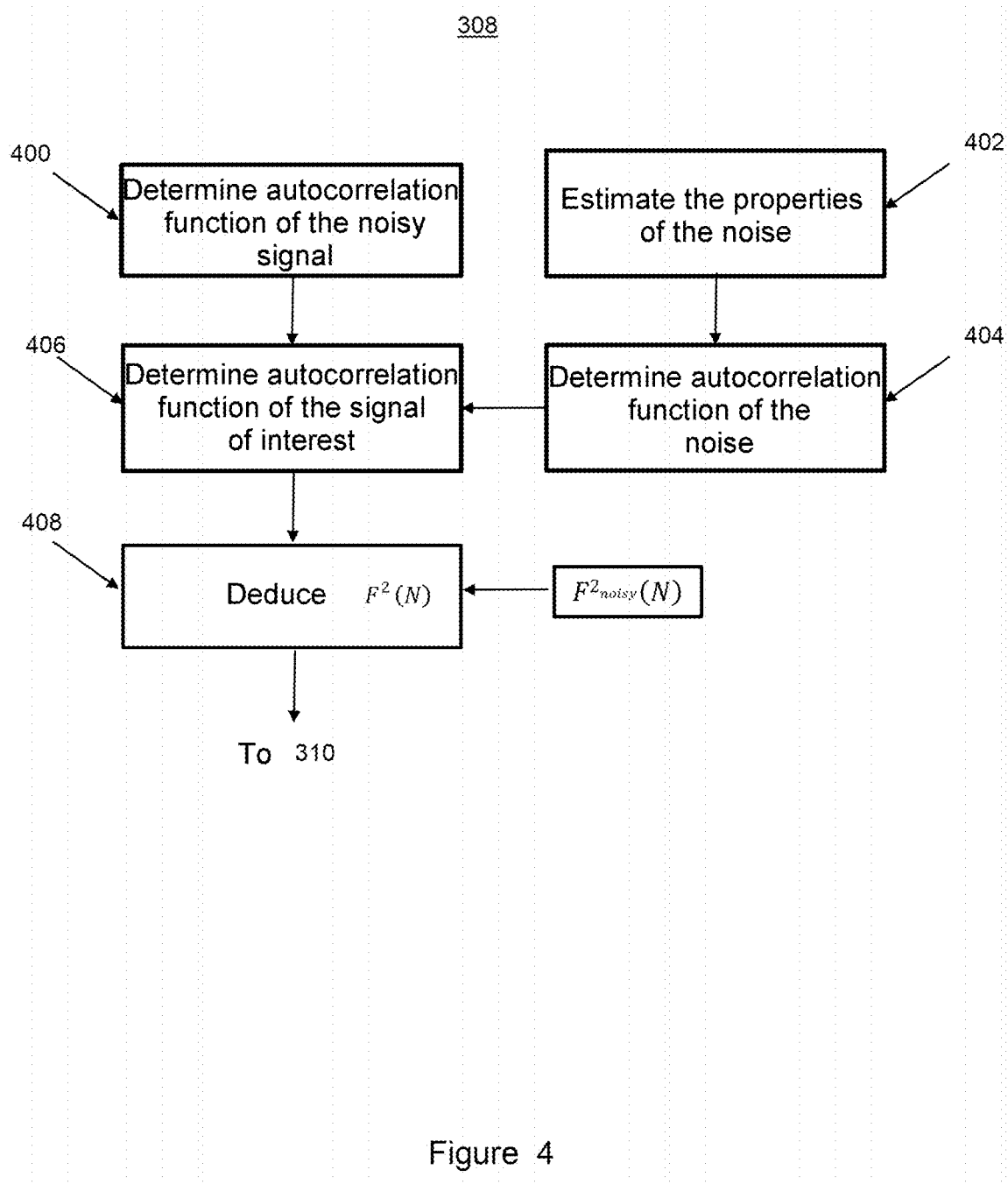
FIG. 4 illustrates a sequence of steps for compensating the influence of noise according to one embodiment of the invention.

FIG. 4 describes the step (308) for deducing the value of the power of the difference between the integrated signal of interest and the trend $\hat{F}^{2}(N)$ with compensation of the influence of noise. In a step (402), the method makes it possible to estimate the properties of the noise, and then to determine (404) the expression of the autocorrelation function of the noise, denoted $R_{b,b}(r)$.

A person skilled in the art understands that the properties of the noise to be estimated may relate for example to the statistical properties and/or the colored or white nature of the noise and/or the parametric model that is able to be formed therefrom, etc.

Based on the autocorrelation function of the noise (404) and on the autocorrelation function of the noisy signal (400), the method makes it possible to determine (406) the autocorrelation function of the signal of interest.

If the noise and the signal are not correlated and wide sense stationary, the autocorrelation function of the noisy signal z is expressed as the sum of the autocorrelation function of the signal of interest y and that of the additive noise b using the following equation:

$$\hat{R}_{y,y}(r) = \hat{R}_{z,z}(r) - \hat{R}_{b,b}(r) \text{ where } r=0, \ldots, LN-1.$$

Then, in a following step (408), the method makes it possible to mathematically compensate the influence of noise in the computation of the value of the power of the difference between the integrated signal of interest and the trend $\hat{F}^{2}(N)$.

The method continues in step (310) in order to estimate the regularity of the signal of interest.

One example is given with white noise: that is to say b a Gaussian white noise with an average of zero and a variance of $\sigma_b^2$. In this case, the noisy signal z is defined as follows:

$$z(n) = y(n) + b(n).$$

Since the autocorrelation function of b is equal to $R_{b,b}(r) = \sigma_b^2 \delta(r)$ with the function $\delta$ defined by:

$$\delta(r) = \begin{cases} 1 & \text{if } r=0 \\ 0 & \text{otherwise} \end{cases},$$

it becomes:

$$R_{y,y}(r) = R_{z,z}(r) - \sigma_b^2 \delta(r).$$

It is then possible to express $F_{\cdot,noisy}^{2}(N)$, the power of the difference between the integrated noisy signal and the estimated trend associated with N, as a function of the power of the difference between the integrated signal of interest and the estimated trend on this same integrated signal of interest associated with N using the equation:

$$F_{\cdot 2}(N) \approx F_{\cdot,noisy}^{2}(N) - Tr(\Gamma_{N,\cdot})\sigma_u^2$$

where $Tr(\Gamma_{N,\cdot})$ is the trace of the matrix $\Gamma_{N}$, i.e. the sum of its diagonal elements.

Figure 6:
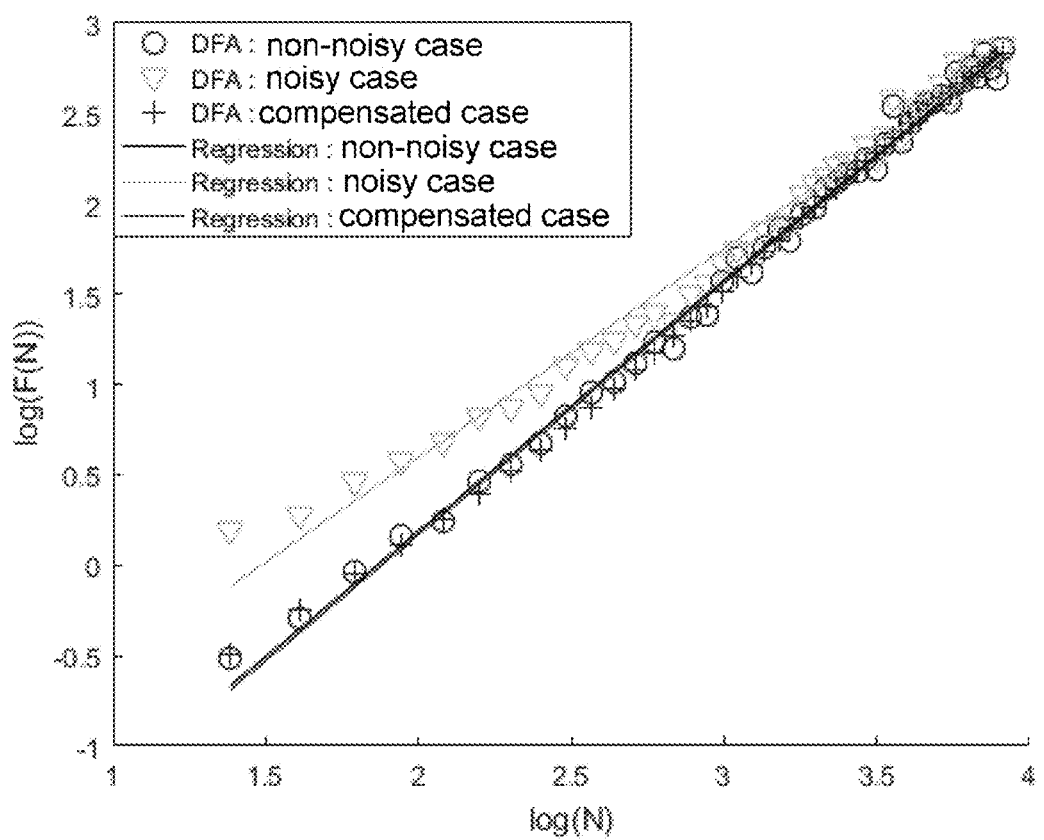
FIG. 6 illustrates the evolution of various values of $\hat{F}^2(N)$ for various values of N using the DFA method and using the method of the invention in a case of a non-noisy signal and of this same noisy signal on a graph log(F(N)) as a function of log(N)

FIG. 6 illustrates the evolution of various values of $\hat{F}^{2}(N)$ as a function of N using the DFA method on a graph $\log(F(N))$ as a function of $\log(N)$. The signal has a regularity estimated as $\alpha=1.60$. By adding noise to this signal by way of white noise having the same power as the signal, it is possible to observe that the noise significantly modifies the value of $F_{noisy}^{2}(N)$ for small values of N. The value of $\alpha$ estimated in the noisy case is therefore changed and is estimated as $\alpha_{noisy}=1.35$. By using the noise compensation method of the present invention, it is possible to eliminate this contribution when computing $\hat{F}_{2}^{2}(N)$, and the estimated value a is improved. In the described case as an example, it has the value: $\alpha_{compensated}=1.61$.

Figure 7:
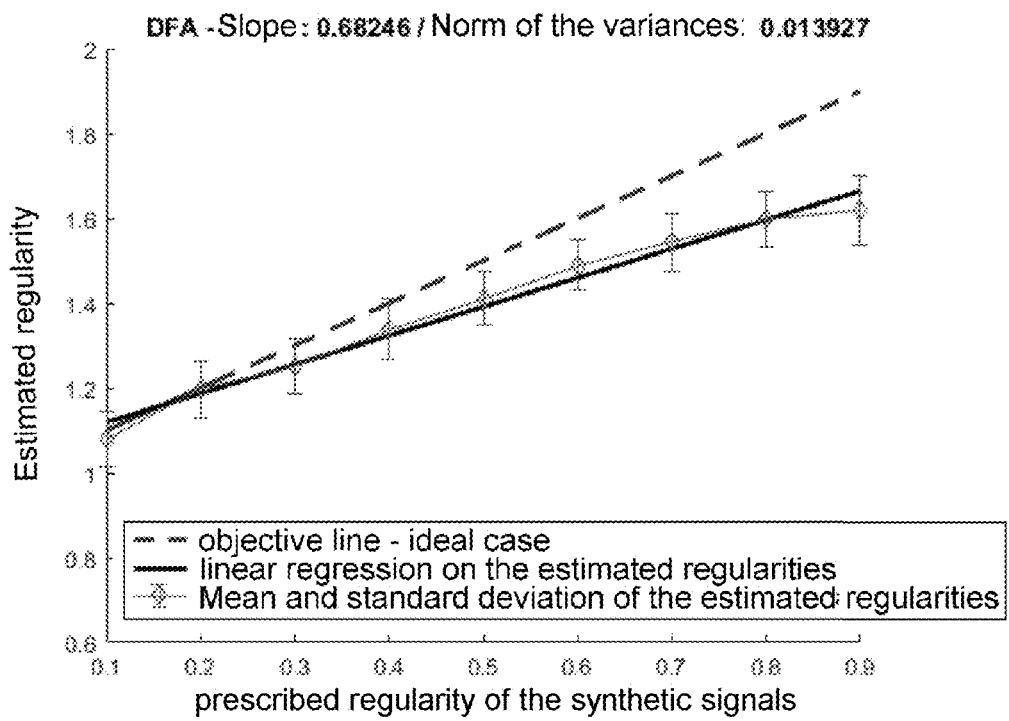
FIG. 7 illustrates comparisons of results obtained using a known enhancement approach and using the method of the invention in the estimation of the regularity of synthetic signals having a known and controlled regularity and that have been disturbed by an additive noise.
Figure 7:
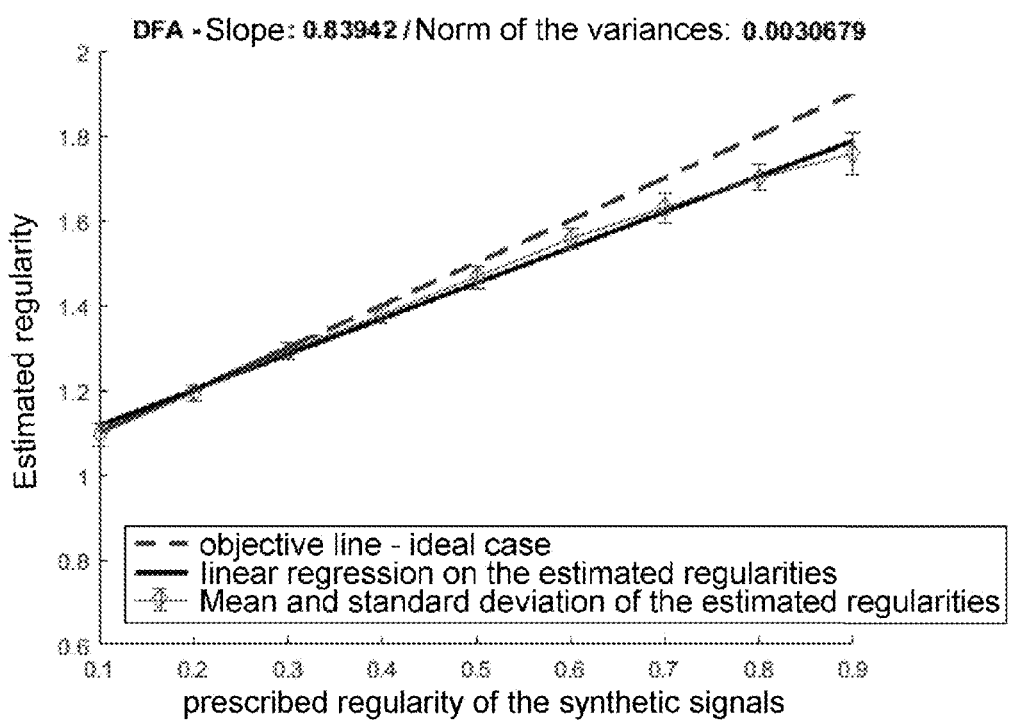

FIG. 7 illustrates comparisons of results obtained for the graph at the top using a conventional approach of enhancing the signal before estimating the regularity, and for the graph at the bottom using the noise compensation method of the invention. The example is shown for 50 synthetic signals whose regularity is known and ranges from 0.1 to 0.9. Noise is then added to these signals by way of white noise whose power is equal to that of the signal.

The curve at the top shows the results when the signals are first of all enhanced and the regularity is then estimated on the enhanced signal or the signal with the noise removed, using a conventional approach. It may then be observed that, for the upper values of a, enhancing a signal changes the estimated regularity value. This phenomenon is accentuated when the a priori regularity of the base signal increases.

The curve at the bottom shows the results with direct noise compensation when estimating the regularity using the method of the invention. It may then be observed that the phenomenon of the estimated regularity value changing is attenuated, and that the method of the invention thus makes it possible to better estimate on average the regularity of a noisy signal.

In addition, the estimation variance with the noise compensation method of the invention is also lower than that obtained with the conventional enhancing approach. Advantageously, it is then possible to accord more trust to the regularity value a estimated on a real signal using the method of the invention than that using known approaches. This method thus makes it possible to more robustly and more accurately estimate the regularity of a signal.

The invention claimed is:

1. A computer-implemented method for determining a state of a system, the method comprising steps of:
   collecting data relating to a system, said data being noisy data comprising data of interest and noise;
   generating a signal to be analyzed from the collected data, said signal being a noisy signal comprising a signal of interest and noise;
   analyzing a regularity of the signal of interest based on the noisy signal by compensating an influence of the noise in the computation of a power of a difference between an integrated noisy signal and its trend; and
   determining the state of said system depending on a result of the analysis of the regularity of the signal of interest estimated from the noisy signal.

2. The method according to claim 1, wherein the step of analyzing the regularity of the noisy signal comprises the steps of:
   defining a set of values of 'N';
   for each value of the set of values of 'N':
   computing a value of the power of the difference between the integrated noisy signal and its estimated trend relative to the value 'N' from an autocorrelation function of the noisy signal;
   computing the value of the power of the difference between the integrated signal of interest and its trend from the difference between the integrated noisy signal and its estimated trend relative to the value 'N' and from an autocorrelation function of the noise; and
   estimating the regularity of the noisy signal.

3. The method according to claim 1, comprising, after the step of generating a signal to be analyzed, a step of computing an autocorrelation function of the noisy signal.

4. The method according to claim 2, wherein the step of computing the value of the power of the difference between the integrated signal of interest and its trend comprises the steps of:
   estimating properties of the noise;
   computing the autocorrelation function of the noise;
   computing the autocorrelation function of the signal of interest from the autocorrelation function of the noise and from the autocorrelation function of the noisy signal; and
   using the autocorrelation function of the noise to mathematically compensate the influence of the noise in the computation of the value of the power of the difference between the integrated signal of interest and its trend.

5. The method according to claim 4, wherein the step of estimating properties of the noise consists in estimating statistical properties and/or a coloured or a white nature of the noise and/or parameters of a parametric model that would be formed from said noise.

6. The method according to claim 2, wherein the step of defining a set of values of 'N' consists in dividing the integrated noisy signal into segments of size 'N' and the step of estimating the regularity of the signal of interest may consist in including the estimation of the trend of said integrated signal for the set of values of 'N'.

7. The method according to claim 2, wherein the step of defining a set of values of 'N' consists in applying a low-pass filter of order 'N' to the integrated noisy signal and the step of estimating the regularity of the signal of interest may consist in including the estimation of the trend of said integrated signal.

8. The method according to claim 1, wherein the step of collecting the data consists in collecting the data from sensors coupled to the system.

9. The method according to claim 8, wherein the sensors are configured so as to collect data relating to an electrical activity of the brain (EEG) "electroencephalogram" and/or to an electrical activity of the heart (ECG) "electrocardiogram" and/or to an electrodermal activity and/or to pupillometry.

10. The method according to claim 8, wherein the sensors comprise at least one inertial sensor that comprises accelerometers and gyrometers.

11. The method according to claim 1, additionally comprising a step of displaying the state of said system depending on the result of the analysis of the regularity of the signal of interest estimated from the noisy signal.

12. A computer program product, said computer program comprising non-transitory code instructions for performing the steps of the method according to claim 1 when said program is executed on a computer.

13. A device for determining a state of a system, the device comprising:
   means for collecting data relating to the system, said data being noisy data comprising data of interest and noise;
   means for generating a signal to be analyzed from the collected data, said signal being a noisy signal comprising a signal of interest and noise;
   means for analyzing a regularity of the signal of interest by compensating an influence of the noise in a computation of a power of a difference between an integrated noisy signal and its trend; and
   means for determining the state of said system depending on a result of the analyzing the regularity of the signal of interest.

14. The device according to claim 13, further comprising a user interface configured to provide the state of the system.

15. The device according to claim 13, wherein the system is an apparatus.

* * * * *